(12) United States Patent
Matsumoto et al.

(10) Patent No.: US 7,181,096 B2
(45) Date of Patent: Feb. 20, 2007

(54) LIGHT WAVEGUIDE AND FLUORESCENT SENSOR USING THE LIGHT WAVEGUIDE

(75) Inventors: Atsushi Matsumoto, Hadano (JP); Shuuji Imuta, Hadano (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/258,210

(22) Filed: Oct. 26, 2005

(65) Prior Publication Data

US 2006/0093262 A1    May 4, 2006

(30) Foreign Application Priority Data

Nov. 1, 2004    (JP) ............................. 2004-318094

(51) Int. Cl.
  *G02B 6/00*    (2006.01)
  *G01N 21/25*    (2006.01)
(52) U.S. Cl. ................... 385/12; 385/37; 250/227.14; 436/172; 356/218; 356/417; 600/317
(58) Field of Classification Search .................. 385/12, 385/31, 32, 37, 49, 131, 147, 902; 356/402, 356/416, 445, 446, 218, 417; 250/227.14, 250/216; 436/164, 165, 172; 600/316, 317, 600/329
See application file for complete search history.

(56) References Cited

U.S. PATENT DOCUMENTS

| 4,755,667 | A | * | 7/1988 | Marsoner et al. ...... 250/227.24 |
| 5,039,490 | A | | 8/1991 | Marsoner et al. |
| 5,137,833 | A | | 8/1992 | Russell |
| 5,157,262 | A | | 10/1992 | Marsoner et al. |

(Continued)

FOREIGN PATENT DOCUMENTS

EP    1 085 315 A1    3/2001

(Continued)

OTHER PUBLICATIONS

S.M. Angel et al.; "Development and Applications of Fiber Optic Sensors", Chemical Sensor Technology, 1991, pp. 163-183, vol. 3 (cited in specification).

(Continued)

*Primary Examiner*—Hemang Sanghavi
(74) *Attorney, Agent, or Firm*—Buchanan Ingersoll & Rooney PC

(57) ABSTRACT

A light waveguide includes: a light introducing portion for introducing light coming from a light source into a waveguide main body; a light radiating surface for radiating the light introduced through the light introducing portion to the hydrogel side; a light transmitting surface which is disposed opposite to and in parallel to the light radiating surface and through which external light incident from the light radiating surface is transmitted to the exterior; a light separation portion, which provided on a surface in a region ranging from the light introducing portion to the light radiating surface and the light transmitting surface, reflecting only totally reflected components of the light introduced through the light introducing portion; an irregular reflection portion provided on the light transmitting surface to change the reflection angle on the light transmitting surface of the light reflected by the light separation portion; and a mirror portion provided at a position opposite to the light introducing portion.

16 Claims, 5 Drawing Sheets

U.S. PATENT DOCUMENTS

| | | |
|---|---|---|
| 5,503,770 A | 4/1996 | James et al. |
| 6,002,954 A | 12/1999 | Van Antwerp et al. |
| 6,011,984 A | 1/2000 | Van Antwerp et al. |
| 6,021,240 A * | 2/2000 | Murphy et al. ............... 385/37 |
| 6,304,766 B1 | 10/2001 | Colvin, Jr. |
| 2002/0164813 A1 | 11/2002 | Colvin, Jr. et al. |
| 2003/0156290 A1 | 8/2003 | Colvin, Jr. et al. |
| 2005/0237518 A1* | 10/2005 | Colvin et al. ............... 356/218 |

FOREIGN PATENT DOCUMENTS

| | | |
|---|---|---|
| JP | 9-061346 A | 3/1997 |
| WO | 99/54714 A1 | 10/1999 |

OTHER PUBLICATIONS

European Search Report dated Mar. 13, 2006.

* cited by examiner

LIGHT WAVEGUIDE AND FLUORESCENT SENSOR USING THE LIGHT WAVEGUIDE

BACKGROUND OF THE INVENTION

The present invention relates to a light waveguide and a fluorescent sensor using the light waveguide.

DESCRIPTION OF THE RELATED ART

Conventionally, a variety of analytical apparatuses have been developed as an apparatus for determining the concentration of an analyte in a liquid. For example, in one of such analytical apparatuses, several milliliters of a solution containing an analyte is put in a transparent vessel having a fixed capacity, the vessel is irradiated with appropriate light, and light absorption or fluorescence of the analyte is measured. This type of analytical apparatus is called a fluorescence spectrophotometer.

The fluorescence spectrophotometer Fluorescence spectrophotometer is so designed that the irradiation axis of an excitation beam is set at 90° against the optical axis of the fluorescence to be measured, and, further, a prism and/or a diffraction grating is used to prevent the wavelength width of the excitation beam from overlapping the wavelength width of the fluorescence to be measured, whereby the signal of the excitation beam is prevented from being added to the signal of the fluorescence. This structure is adopted for obviating the problem that, upon incidence of the excitation beam on a photodetector for detecting the fluorescence, a signal from the excitation beam would be added as a bias to the fluorescence varying depending on the analyte, so that the variation in the signal corresponding to the variation in the analyte concentration would be relatively reduced, resulting in worsening of the response.

Meanwhile, for obtaining a sensor which is suited to determination of an analyte in blood in an amount on a microliter level or which can be constantly connected to or embedded in a living body, reductions in size and power consumption are important factors. However, the fluorescence spectrophotometer is complicated in configuration and, therefore, cannot be reduced to such a size as to be constantly connected to or embedded in a living body.

In view of this, researches for reducing the size of a measuring instrument (sensor) for a tiny amount of liquid sample have been made.

For example, there is an apparatus miniaturized for the purpose of measuring glucose in a humor inside a living body. Such miniaturized sensors include a sensor for measuring penicillin in a tiny amount of solution by using enzyme as a molecule recognition material and using an optical fiber (see S. M. Angel et al., "Development and Applications of Fiber Optic Sensors", Chemical Sensor Technology, 3 (1991), pp. 163–183).

In this sensor, penicillinase as an enzyme and fluorescein as a fluorescent coloring matter are fixed on an end face of an optical fiber having a diameter of 250 µm, and decomposition of penicillin by penicillinase takes place if penicillin is present in the vicinity thereof. The hydrogen ion generated upon this reaction causes a pH variation, the variation in the intensity of fluorescence of fluorescein generated due to the pH variation is guided through the optical fiber and read by a photodetector, and the amount of penicillin is measured. In the measurement using this sensor, however, it is difficult to homogeneously form an enzyme fixation film at the tiny optical fiber tip end, and the fluorescent light is diffused not only in the optical fiber direction but also in all directions, so that the fluorescent signal obtained is very small, and the photodetector needs to have a high amplification coefficient, as can be easily supposed.

In addition, other sensors include a sensor using a flat plate-like light waveguide (flat plate light waveguide). The sensor using the flat plate light waveguide is an immune sensor utilizing an antigen-antibody reaction. Further, there are light waveguide type biosensors using a flat light waveguide as an oxygen sensor or an ion sensor.

Besides, other sensors using a flat light waveguide include a sensor in which a film with glucose oxidase fixed thereto is placed on the flat light waveguide, and an argon laser beam is guided in the waveguide (Japanese Patent Laid-open No. Hei 9-61346). This sensor measures the concentration of glucose with high sensitivity by use of the effect in which FAD as a coenzyme in glucose oxidase absorbs evanescent waves generated by the argon laser beam, to fluoresce.

This sensor, however, has difficulties in reducing the size of the argon laser utilized. For example, it is difficult to achieve reductions in size and power consumption of an argon laser, as compared with the case of LED, and there is a limitation to reduction in overall size of the sensor inclusive of an optical system. Besides, the evanescent waves can only excite FAD in a thickness corresponding roughly to the wavelength, at the surface of the sensor, so that only faint fluorescent light is obtained.

Meanwhile, it is known in the field of treatment of diabetes that self-control of the patient's glucose level to within a normal range is important for preventing complications such as retinopathy and nephropathy. Therefore, endeavor to develop a method for continuously measure the glucose concentration in a living body has been made for many years. It can be easily supposed that, for such a purpose, it is effective to adopt a system in which a detector having an indicator layer showing a variation in fluorescent characteristics by reacting with glucose reversibly is embedded in a living body, the glucose concentration is measured based on the variation in the amount of fluorescence, and the data is led out of the living body by electromagnetic waves or the like.

As a member which can be utilized for the indicator layer for attaining the purpose, there has been proposed a member in which a fluorescent substance capable of reversibly coupling with glucose, such as phenylboronic acid, is bonded to polystyrene through covalent bond (U.S. Pat. No. 5,137,833).

In addition, there have been a proposal as to a fluorescent substance capable of reversely bonding specifically to glucose among the various sugar components present in the living body components (U.S. Pat. No. 5,503,770), a proposal relating to smaller types of light source and detector which can be easily embedded in a living body (U.S. Pat. No. 5,039,490), and the like.

Until now, however, there has not yet been realized an apparatus by which the glucose concentration in a living body can be monitored accurately, continuously and for a long time.

In fluorometry, generally, the amount of fluorescent light discharged from a fluorescent substance is very small as compared with the amount of the excitation beam, and, therefore, it is important to minimize the amount of the excitation beam incident on the photodetector. As such a sensor, there has been proposed a tiny sensor in which a light source, a photodetector, and an indicator layer to be varied in optical characteristics by an analyte are integrally laminated on one another utilizing a photolithography (U.S. Pat.

No. 5,157,262). The photodetector-light source integral type sensor has been tried to devise and investigated for many years as a structure promising a reduction in size to such an extent as not to be realized by the prior art. In practice, however, stray light or the like due to the reflection arising from the difference in refractive index between layers or due to the reflection of light on wirings for supplying electric power to the LED (light source) and the photodetector is liable to be incident on the photodetector, and, even when an optical filter is used, the structure is difficult to realize for a sensor for measuring with high sensitivity the fluorescence which is faint relative to the excitation beam.

As a further sensor, there has been proposed a small type sensor structure in which an LED and a photodetector are arranged and a screen is disposed therebetween so that the light from the LED cannot be directly incident on the photodetector (U.S. Patent Application No. 2003/0156290). This sensor is free of light irregularly reflected by electric wiring or the like, is effective for reducing stray light, and can detect the fluorescent component with high sensitivity.

However, in such a small type sensor, the fluorescent light from the indicator layer located on the sensor surface is faint diffused light, and it is therefore apparent that the minimization of the spacing between the photodetector surface and the indicator is effective for measuring the glucose concentration in a living body with high accuracy. In this proposal, however, an angle must be formed between the direction of the LED light and the direction of the fluorescent light going toward the photodetector, so that a spacing for intersection of light beams must be provided between the LED and the photodetector and the sensor surface including the fluorescence indicator, resulting in that the overall size of the sensor would be enlarged and the efficiency of fluorescence detection might be worsened.

SUMMARY OF THE INVENTION

In consideration of the foregoing, it is an object of the present invention to provide a light waveguide such that fluorescence can be excited efficiently while suppressing the stray light arising from reflection of an excitation beam and that the fluorescent light generated can be efficiently guided to a photodetector.

It is another object of the present invention to provide a fluorescent sensor reduced in size to such an extent that the sensor can be utilized as an embedded-in-body type sensor, by use of this waveguide.

In order to attain the above first object, according to the present invention, there is provided a light waveguide included of a light transmitting material, the light waveguide including: a light introducing portion for introducing light coming from a light source; a light radiating surface for radiating the light introduced through the light introducing portion; a light transmitting surface which is opposed to the light radiating surface and through which at least a portion of external light incident from the light radiating surface is transmitted to the exterior; an irregular reflection portion provided on the light transmitting surface to change the reflection angle of light on the light transmitting surface; and a light separation portion provided on a surface in a region ranging from the light introducing portion to the light radiating surface and the light transmitting surface, the light separation portion having an absorption layer formed of a material having a refractive index lower than the refractive index of the light transmitting material and higher than the refractive index of a material in contact with the light transmitting surface.

Besides, in order to attain the above another object, according to the present invention, there is provided a fluorescent sensor including: the above-mentioned light waveguide; a light source for radiating an excitation beam to a light introducing portion of the light waveguide; an indicator layer provided in close contact with a light radiating surface of the light waveguide and including a hydrogel containing fluorescent indicator molecules which show a variation in fluorescent characteristics by reversibly bonding with an analyte; and a photo-detector provided at a position opposite to the light transmitting surface of the light waveguide for converting fluorescent light from the indicator layer into an electrical signal.

BRIEF DESCRIPION OF THE DRAWINGS

DETAILED DESCRIPTION OF THE PREFERRED EMBODIMENTS

The embodiments of this invention will be described below with reference to the accompanying drawings.

[Light Waveguide]

Figure 1:
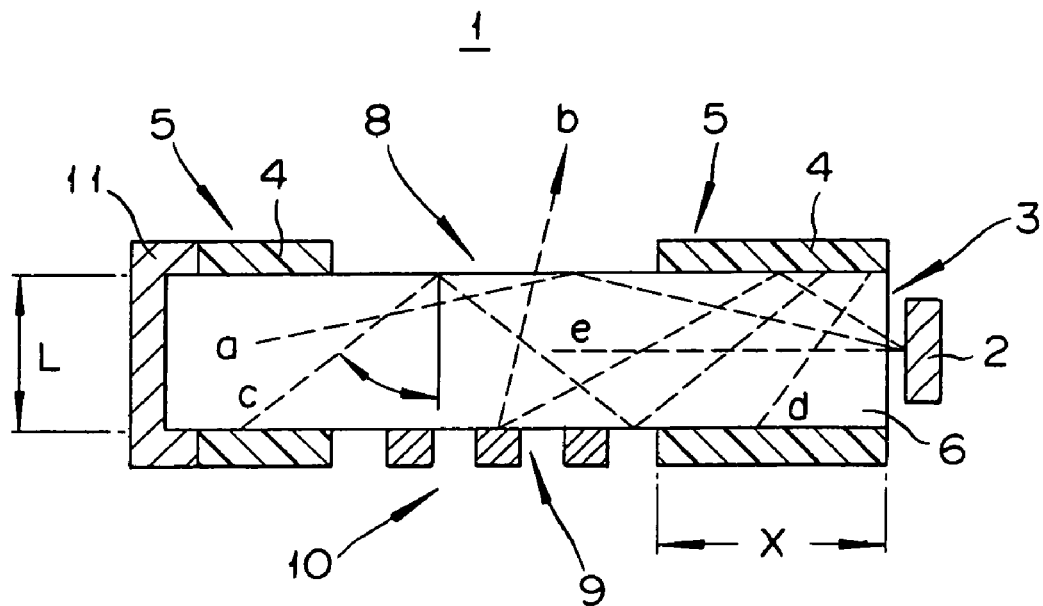
FIG. 1 is a sectional view for illustrating a light waveguide to which the present invention is applied.
Figure 2A:
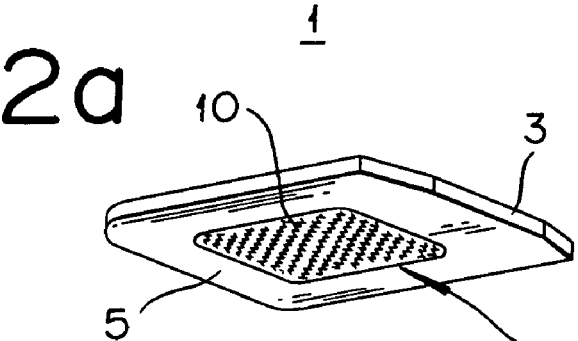
FIGS. 2A and 2B are perspective views for illustrating the light waveguide.
Figure 2B:
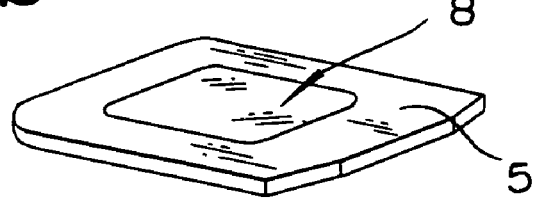

FIG. 1 is a sectional view for illustrating one example of the light waveguide according to the present invention, and FIGS. 2A and 2B are perspective views of the light waveguide, in which FIG. 2A shows the light transmitting surface side and FIG. 2B shows the light radiating surface side so that the configurations on both sides of the light waveguide can be seen.

The light waveguide 1 is based on a waveguide main body 6 which is flat plate-like in shape and is formed of a transparent light transmitting material through which both an excitation beam and fluorescent light can be transmitted.

The waveguide main body 6 includes: a light introducing portion 3 for introducing light from a light source 2 such as an LED into the waveguide main body 6; a light radiating surface 8 for radiating the light introduced through the light introducing portion 3; a light transmitting surface 9 which is located opposite to and in parallel to the light radiating surface 8 and through which at least a portion of external light incident through the light radiating surface 8 is transmitted to the exterior; an irregular reflection portion 10 provided on the light transmitting surface 9 for changing the reflection angle of light on the light transmitting surface 9; a light separation portion 5 which is provided on a surface ranging from the light introducing portion 3 to the light radiating surface 8 and the light transmitting surface 9 and which has an absorption layer 4 formed of a material lower in refractive index than the waveguide main body 6 and higher in refractive index than a material in contact with the light transmitting surface 9; and a mirror portion 11 provided at a position opposite to the light introducing portion 3. In addition, the waveguide main body 6 is provided with a light separation portion 5 also in the range from the light radiating surface 8 and the light transmitting surface 9 to the mirror portion 11.

The light waveguide 1 is used, for example, for a fluorescent sensor for measuring, and continuously determining, an analyte present in a living body and showing fluorescent or an analyte optically inactive but varied in fluorescent characteristics by coupling with indicator molecules. The detailed structure of such a fluorescent sensor will be described later. Incidentally, the fluorescent sensor has a general structure in which a light source 2 is disposed on the side of a light introducing portion 3 of the waveguide 1, a light radiating surface 8 is disposed on the side for contact with a liquid containing an analyte, and a photodetector is disposed on the side of a light transmitting surface 9. A space with a low refractive index is provided between the light transmitting surface 9 and the photodetector. The space with a low refractive index is formed depending on the material constituting the waveguide main body 6; in the case where the waveguide 6 is formed of a solid substance being transparent, ordinarily, the space is filled with an inert gas such as nitrogen gas or air having a refractive index of around 1. The space in contact with the waveguide main body 6 is filled with air or a nitrogen gas, and the space can be set to have a predetermined refractive index; therefore, such a space will also be referred to as a material hereinafter.

The waveguide main body 6 can be freely designed according to, for example, the size of the fluorescent sensor and/or the quantity of the light guided, and its thickness is about 10 μm to 3 mm, for example.

The relationships of $n1>n2+0.01$ and $n2>n3+0.01$ are satisfied, where $n1$ is the refractive index of the waveguide main body 6 (light transmitting material), $n2$ is the refractive index of the absorption layer 4, and $n3$ is the refractive index of the material in contact with the light transmitting surface 9. This makes it possible to prevent the problem that the light component not undergoing total reflection, of the light incident through the light introducing portion 3, would leak out through the light transmitting surface 9 to be incident on the photodetector, thereby hindering the intended measurement of fluorescence. Incidentally, the relationships are preferably $n1>n2+0.1$ and $n2>n3+0.1$.

Besides, the distance X over which the light separation portion 5 is located in the range from the light introducing portion 3 to the light radiating surface 8 and the light transmitting surface 9 can be expressed as $X = t1 \times L \times \text{Tan}(\text{Sin}^{-1}(n2/n1))$, where L is the thickness of the waveguide main body 6, $n1$ is the refractive index of the waveguide main body 6, and $n2$ is the refractive index of the absorption layer 4. In this case, t1 must have a value of greater than 1, preferably greater than 3, and more preferably greater than 5. Incidentally, the upper limit of the value can theoretically be enlarged within the distance that the light can reach; in practice, however, the value is designed in consideration of the arrangement inside the fluorescent sensor. In view of specific design, t1 is preferably not more than 1000. In addition, the length of the light separation portion 5 is preferably 5 to 10 times the thickness of the waveguide main body 6. Incidentally, the distance of the light separation portion 5 in the range from the light radiating surface 8 and the light transmitting surface 9 to the mirror portion 11 also preferably satisfies the above-mentioned formula in the same manner as the above-mentioned light separation portion 5, but the values for the different light separation portions 5 may not necessarily be equal.

The blank material for the waveguide main body 6 may be any blank material inasmuch as it can transmit light to such an extent as not to spoil the functions of the excitation beam for the fluorescence utilized in the fluorescent sensor and of the fluorescent sensor. Preferable examples of the blank material include glasses such as synthetic quarts, borosilicate glass, etc. and plastics such as acrylic resin, polystyrene, polycarbonate, cyclic polyolefins, etc. The refractive index of each of these blank materials must at least be higher than the refractive index of the material in contact with the light radiating surface 8, i.e., the liquid containing the analyte or a hydrogel containing the liquid and the refractive index of the absorption layer 4; for example, the refractive index of the blank material is preferably not less than 1.45.

The light radiating surface 8 is present at one surface of the waveguide main body 6. Similarly, the light transmitting surface 9 is at another surface of the waveguide main body 6. The light radiating surface 8 and the light transmitting surface 9 are formed in parallel at opposite positions, with the waveguide main body 6 therebetween, i.e., with the portion through which the light is guided therebetween, so that most of the light incident through the light radiating surface 8 can reach the photodetector in the fluorescent sensor by passing through the light transmitting surface 9 without being reflected inside the waveguide main body 6.

The light introducing portion 3 is also present at one surface of the waveguide main body 6. Let the one surface be a light introducing surface, then it suffices for the light introducing surface to be a surface through which the light from the light source 2 can be incident on the inside of the waveguide main body 6 and which ensures that at least a portion of the incident light can be totally reflected at the light separation portions 5, and the light introducing surface may be a surface vertical to, or inclined relative to, the light radiating surface 8 and the light transmitting surface 9.

In addition, a portion of the light separation portion 5 may be formed to be free of the absorption layer 4, this portion may be provided with a recessed portion or a through-hole, and the excitation beam may be introduced through this portion.

The absorption layer 4 is formed of a material having a refractive index higher than the refractive index of the material in contact with the light transmitting surface 9; for example, where the material in contact with the light transmitting surface is air, the absorption layer 4 may be formed of a fluoro-resin. Specifically, the light incident through the light introducing portion 3 impinges on the interface between the waveguide main body 6 and the fluoro-resin at various angles, and, while the light is repeatedly reflected by the light separation portions 5, the light reflected at other angles than the total reflection angle is radiated out of the waveguide main body 6, whereas the totally reflected components are supplied to the irregular reflection portion 10.

In the case where the light other than the reflected components leak out through the separation portions 5 to the surroundings of the waveguide main body 6, it is high possible that the light radiated to the exterior may undergo irregular reflection inside a housing of the fluorescent sensor described later, to be again incident through the light radiating surface 8 and the light separation portions 5 and to be incident as it on the photodetector through the light transmitting surface 9 as stray light. The stray light thus incident causes a conspicuous lowering in the detection sensitivity of the fluorescent sensor. Such incidence of the stray light can be prevented by protecting the light radiating surface 8 and the light transmitting surface 9 from the stray light by an appropriate method (for example, by covering the inside of the housing with a light-absorptive coating and partitioning the surroundings of the light radiating surface with walls so as to optically intercept the stray light).

The absorption layers 4 of the light separation portions 5 at the surfaces of the waveguide main body 6 can be formed of a material containing a light-absorbing coloring matter. Such absorption layers 4 prevent the light other than the totally reflected components from leaking out through the light separation portions 5, and absorb the light other than the totally reflected components which has leaked out through the light absorption portions 5 of the waveguide main body 6. Therefore, with the absorption layers 4 provided, substantially only the totally reflected components, of the light introduced through the light introducing portion 3, can be guided and supplied to the irregular reflection portion 10.

In addition, since the waveguide main body 6 is provided with the absorption layers 4 containing the coloring matter, it is ensured that even if a stray light component should be present inside the housing, the stray light can be prevented from entering into the waveguide main body 6.

The blank material of the absorption layers 4 is preferably a fluoro-resin containing a highly light-absorptive compound, for example. Besides, as the difference in refractive index between the waveguide main body 6 and the absorption layers 4 is greater, the light from the light source 2 is guided more efficiently. Therefore, the absorption layers 4 are preferably formed of a material such that the difference in refractive index between the material and the waveguide main body 6 is not less than 0.01, preferably not less than 0.1.

As for the combination of materials, in the case where a glass or resin having a refractive index of not less than 1.5 such as borosilicate glass and acrylic resin and polycarbonate is used for the waveguide main body 6, more preferable examples of the material for the absorption layers 4 include fluoro-resins such as polytetrafluoroethylene (PTFE), tetrafluoroethylene-perfluoroalkyl vinyl ether copolymers (PFA), tetrafluoroethylene-hexafluoropropylene copolymer (FEP), tetrafluoroethylene-ethylene copolymer (ETFE), polychlorotrifluoroethylene (PCTFE), polyvinylidene fluoride (PVDF), and amorphous fluoro-resins, having a refractive index of about 1.3 to 1.43.

Resin films in which a few percent of a coloring matter capable of absorbing the waveguided light is mixed into the above-mentioned blank material may be adhered to the waveguide main body 6 as the absorption layers 4, or the absorption layers 4 may be formed by mixing the coloring matter into the amorphous fluoro-resin dissolved in a solvent, applying the resultant mixture to the waveguide main body 6, and drying the applied mixture.

Besides, in the case where synthetic quartz with a refractive index of about 1.46 is used, an amorphous fluoro-resin having a refractive index of 1.34 and admixed with an appropriate proportion of the coloring matter is preferably used.

As the coloring matter here, there can be used dye-based and pigment-based coloring matters which are used for printing; among them, preferred is carbon black capable of absorbing a wide wavelength range of light.

It suffices for the thickness of the absorption layer 4 to be on such a level that the light to be guided cannot be transmitted through the absorption layer 4 and the external stray light cannot enter into the waveguide main body 6; specifically, the absorption layer 4 preferably has a light transmittance of 0.01% or below. Therefore, the thickness of the absorption layer 4 can be controlled within the range of about 10 to 1000 µm, though it differs depending on the blank materials of the above-mentioned portions. Particularly, in the case of a fluoro-resin admixed with 5% of carbon black, a layer thickness of 20 µm ensures that the amount of stray light entering into the waveguide main body 6 can be controlled to 0.01% or below.

In addition, on the absorption layer 4 may be molded recesses and/or projections to be utilized for positioning relative to a window portion of the housing (described later), the photodetector and the like.

The irregular reflection portion 10 is provided for radiating the light, guided from the light source 2, through the light radiating surface 8 so that the excitation beam is radiated to the side of the analyte-containing liquid.

Figure 3:
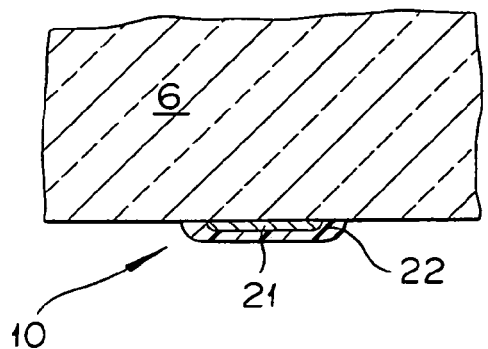
FIG. 3 is a sectional view showing the structure of an irregular reflection portion.

FIG. 3 is a sectional view showing the structure of the irregular reflection portion 10.

The irregular reflection portion 10 is composed of a particulate mixed transparent layer 21 in which a transparent material higher in refractive index than the waveguide main body 6 is admixed with particulates different in refractive index from the transparent material, and a reflection layer 22 disposed so as to hide the particulate mixed transparent layer 21 from the exterior.

Such a irregular reflection portion 10 can be produced on the light transmitting surface 9 by applying a transparent coating material (transparent material) having a high refractive index and containing reflective particulates to the light transmitting surface 9, drying the transparent coating material to form the particulate mixed transparent layer 21, then applying to the outside of the dried transparent coating an opaque coating material (opaque material) to be the reflection layer 22, so as to cover the transparent coating, and drying the opaque coating material to form the reflection layer 22.

As the transparent coating material, there is used a material having a refractive index equal to or higher than that of the waveguide main body 6. For example, where the waveguide main body 6 is formed of quartz glass, an acrylic coating material or the like is preferably used as the transparent coating material. The particulate mixed transparent layer 21 may be formed by a method in which a coating material commercially available in a doped form containing the acrylic resin dissolved in a solvent such as a UV-curing resin is admixed with titanium oxide, alumina or metallic particulates or hollow glass particulates having a high refractive index as the reflective particulates, and the admixture is applied to the surface of the waveguide main body in the form of dots or pattern-printed on the surface by an ink jet system, relief printing or the like. On the outside surfaces of the dots thus formed, printing is again conducted using an opaque printing ink containing carbon black or metallic particulates, to produce the reflection layer 22. Incidentally, the reflective particulates in the particulate mixed transparent layer 21 may be bubbles.

At the irregular reflection portion 10, when the light guided inside the light waveguide 1 at incidence angles greater than the total reflection angle is incident on the particulate mixed transparent layer 21, the light cannot undergo total reflection because the refractive index of the irregular reflection portion 10 is high, and the light enters into the particulate mixed transparent layer 21, to be reflected or refracted by the particulates having a greatly different refractive index. A portion of the light thus reflected or refracted, attended by such incidence angles that it cannot undergo total reflection inside the waveguide main body 6, is again radiated from the irregular reflection portion 10 into the waveguide main body 6. As a result, an excitation beam is radiated from the light radiating surface 8 to the side of the analyte-containing liquid.

Meanwhile, the fluorescent component radiated from the light radiating surface 8 and transmitted through the light transmitting surface 9 to be incident on the photodetector is diffused light. Therefore, in order to detect the fluorescence with high sensitivity, it is important that the distance from the indicator layer (detailed later) provided on the light radiating surface 8 to the photodetector is as short as possible and that the fluorescent energy can be transmitted to the photodetector side through an area which is as wide as possible, as compared with the distance. Therefore, it is important that the areas of the light radiating surface 8 and the light transmitting surface 9 are set to be as wide as possible so as to accommodate a distance of not less than several to several tens of times the thickness L of the waveguide main body 6. In this embodiment, the distance from the fluorescent indicator to the photodetector can be reduced to a distance of ten and a few micrometers, which is a value obtained by adding the thickness of the irregular reflection portion 10 to the minimum thickness of 10 μm of the waveguide main body 6. Therefore, a sensor capable of efficiently transmitting the fluorescent energy to the photodetector, notwithstanding its small size, can be realized.

The irregular reflection portion 10 may assume any of various shapes such as round, elliptic, linear, meshed and the like shapes. From the viewpoints of enhancement of efficiency of fluorescence detection and a reduction in size, however, it is preferable that the irregular reflection portions 10 are dispersed on the light transmitting surface 9 so that the excitation beam is evenly radiated through the light radiating surface 8.

Figure 4:
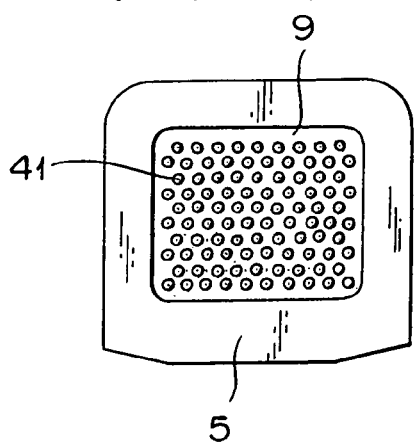
FIG. 4 is a plan view showing an example of the layout pattern of the irregular reflection portion.
Figure 5:
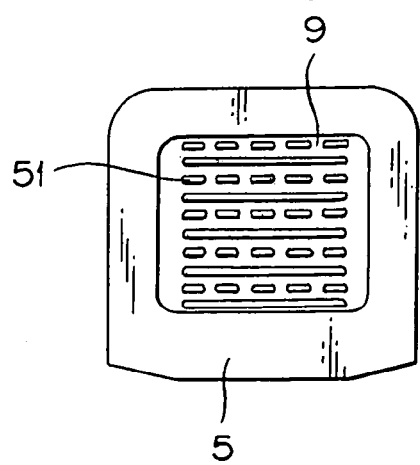
FIG. 5 is a plan view showing another example of the layout pattern of the irregular reflection portion.

FIGS. 4 and 5 are plan views showing examples of the layout pattern of the irregular reflection portion 10.

In order to evenly radiate the excitation beam through the light radiating surface 8, it may be contemplated to adopt, for example, a pattern consisting of a plurality of circular dots as shown in FIG. 4, or a pattern consisting of a combination of rectangular dots 51 as shown in FIG. 5.

Such a pattern may have a configuration in which the dots 41 or the rectangular dots 51 constitute the irregular reflection portion 10, or a configuration in which the dots 41 or the rectangular dots 51 are light-transmitting portions and the other portions constitute the irregular reflection portion 10.

In the case where the dots 41 or the rectangular dots 51 constitute the irregular reflection portion 10, it is effective that any dots on the light transmitting surface 9 other than the irregular reflection portion 10 are not spaced apart from each other than at least the value represented as $2 \times L \times \mathrm{Tan}(\mathrm{Sin}^{-1}(n4/n1))$, i.e., the distance between the irregular reflection portions in the irregular reflection portion 10, the value being preferably smaller than $L \times \mathrm{Tan}(\mathrm{Sin}^{-1}(n4/n1))$, where n4 is the refractive index of the material which is in contact with the light radiating surface 8 and which contains the fluorescent indicator. This ensures that the excitation beam is evenly radiated through the light radiating surface 8. Incidentally, this discussion applies also to the case where the dots 41 or the rectangular dots 51 are transparent portions capable of transmitting fluorescent light therethrough and the other portions constitute the irregular reflection portion 10. Besides, this discussion holds irrespectively to the shape of the dots. The specific numerical value varies depending on the refractive index of the waveguide main body 6 and the refractive index of the indicator layer in contact with the light radiating surface 8; a generally preferred numerical value is within 5 times the thickness L of the waveguide main body 6, more preferably within 2 times the thickness L.

On the other hand, the proportion of the irregular reflection portion 10 based on the whole area of the light transmitting surface 9 is not particularly limited, but, generally, it is preferably set to be as small as possible, say, in the range of 50% to 0.1%, more preferably in the range of 20 to 1%. The proportion may be set according to the amount of the excitation beam guided, the efficiency of the irregular reflection portion 10, or the ratio of the fluorescent light to the excitation beam at the fluorescent indicator which is an object of measurement as the sensor; for example, in the case of a sensor having pluralities of light radiating surfaces 8 and light transmitting surfaces 9, what percent of the excitation beam guided should be radiated through each light radiating surface 8 for enabling efficient measurement through the plurality of light transmitting surfaces 9 may be set as an appropriate value on the basis of designing of the fluorescent sensor.

Besides, the areas and shapes of the light radiating surface 8 and the light transmitting surface 9 are determined according to the size of the photodetector used and/or the balance of the fluorescent signal obtained, and are not particularly limited. For example, sizes and shapes ranging from a circle with a diameter of about 50 μm to a square with a side length of about 10 mm may be adopted.

Here, another form of the irregular reflection portion 10 will be described.

The incidence angle of the light guided by the light waveguide 1 on the surface of the waveguide main body 6 is not less than about 45 degrees in general configurations. Therefore, for efficient irregular reflection of the light being guided, the particulate mixed transparent layer 21 may be formed by applying a coating material with a high refractive index to the light transmitting surface 9 as above-mentioned, or an irregular reflection portion 10 recessed into the waveguide main body 6 relative to the light transmitting surface 9 of the waveguide main body 6 may be provided. In the latter case, irregular reflection of more light can be achieved, as compared with the former case.

Figure 6:
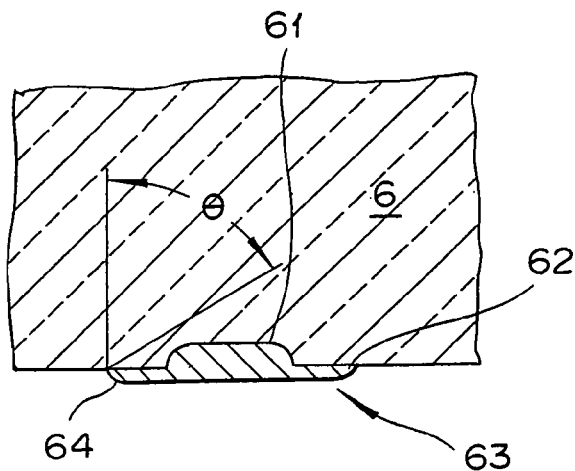
FIG. 6 is a sectional view showing the structure of another embodiment of the irregular reflection portion.

FIG. 6 is a sectional view showing the structure of another form of the irregular reflection portion 10.

The irregular reflection portion 10 is constituted of dots 63 each of which consists of one recessed portion 61 and a flange portion 62 disposed in the periphery thereof.

The flange portion 62 is in contact with the surface of the waveguide main body 6, and the contact surface is optically flat, in the same manner as the waveguide main body 6. The recessed portion 61 is recessed into the inside of the waveguide from the surface of the waveguide main body 6. Here, the recessed portion 61 and the flange portion 62 are so produced that a straight line drawn at a minimum incidence angle θ of the excitation beam being guided against the normal drawn from an end portion 64 of the flange portion 62 perpendicularly to the waveguide main body 6 would not make contact with the recessed portion 61 in any case.

Of the excitation beams irregularly reflected in various directions by the recessed portions 61, the beams reflected at such angles as to enable wave guiding through total reflection inside the waveguide main body 6 cannot be radiated through the light transmitting surface 9, in the same manner as the wave-guided light. However, the beams irregularly reflected at other angles can be radiated through the light radiating surface 8 if they are directed to the side of the light radiating surface 8; on the other hand, the beams directed to the side of the light transmitting surface 9 are necessarily reflected by the flange portions 62, and are radiated through the light radiating surface 8 or absorbed by the light separation portions 5, so that they cannot be radiated through the light transmitting surface 9. As a result, the scattered light components would not be radiated directly through the light transmitting surface 9 to be incident on the photodetector. Accordingly, the dots 63 including the flange portions 62 function as a reflection portion.

Such dots 63 are formed of a material liable to reflect light, and can be produced by printing in which a commercially available glossy coating material or the like is used. For example, a finer irregular reflection portion 10 can be realized by use of a laser micro-machining technology or a photolithographic technology which have been remarkably advanced in recent years.

Here, description will be made of an example of production of an irregular reflection portion 10 in which a glass is used to form the waveguide main body 6. In producing the irregular reflection portion 10, first, a UV-curable resin is applied to a glass plate by spin coating or the like, light exposure in a desired pattern is conducted, and the other areas than the areas for formation of recessed portions 61 are masked with a resin. Next, by use of a reactive ion etching apparatus, etching is conducted while introducing carbon fluoride, to produce the recessed portions 61 in the non-masked areas.

After the masking agent is removed by polishing, hot phenol or the like, a metal capable of efficiently reflecting the wave-guided light, such as aluminum and silver, is applied to the whole area of the light transmitting surface by sputtering or vapor deposition. In this case, the metallic portion must have such a thickness as not to transmit light therethrough, and the thickness is desirably not less than 2 times the wavelength of the excitation beam to be waveguided, and not less than 1 μm. Where the desired thickness cannot be obtained by only vapor deposition or sputtering, the thickness may be further increased by a plating treatment. A UV-curable resin is applied by spin coating or the like to the whole area of the light transmitting surface coated with the metal, followed by UV exposure, to produce a pattern covering the flange portions 62 and the recessed portions 61, and washing is conducted to remove the uncured UV-curable resin. Finally, the exposed metallic portions are removed by an acid or electrolysis, to obtain a pattern of dots 63.

Incidentally, the recessed portions 61 can be produced also by etching in which excimer laser or YAG laser is used, without masking. Where the diameter of the recessed portions 61 is designed to be large, the recessed portions 61 can be produced also by mechanical cutting by use of sandblast or a drill.

Where the light waveguide 1 is made of a plastic, by use of the technology utilized in the production of compact disks, a male type mold is produced by use of the glass wafer provided with the recessed portions 61 as an electroforming mold, and, by use of the male type mold as a press mold, the recessed portions 61 is transferred to a thermoplastic resin film, whereby the irregular reflection portion 10 can be produced. Further, after vapor deposition of a metal is conducted in the same manner as in the case of the glass-made light waveguide, only the irregular reflection portion 10 is coated with a mask by photolithography, and the metallic film portion in the surroundings of the irregular reflection portion 10 is removed by an acid or electrolysis, whereby the light waveguide 1 can be produced.

In the case of such a production method, a very fine irregular reflection portion 10 can be produced, as compared with the case of producing the dots 63 by the coating as above-mentioned. For example, in the case of producing a circular irregular reflection portion 10, the printing method leads to a diameter of about 0.2 mm at minimum, but the use of photolithography makes it possible to realize a diameter of around 1 μm. However, for efficient irregular reflection of the excitation beam, it is meaningless to reduce the size of the recessed portions 61 more than required. Where the recessed portions 61 are cylindrical in shape, both the minimum diameter and the depth thereof are preferably not less than 2 times the excitation beam wavelength, and, on the basis of function, an appropriate diameter is about 1 to 300 μm, and an appropriate depth is 1 to 100 μm.

On the other hand, the portions liable to cause irregular reflection of light are the edge portions of the recessed portions 61 or those portions of the bottom surface and the side surfaces which are not parallel to or vertical to the light transmitting surface 9. Therefore, production of such portions at the inside surfaces of the recessed portions 61 in a number as great as possible promises efficient irregular reflection. Therefore, in the case where the thickness L of the waveguide main body 6 is comparatively large, for example, not less than about 0.5 mm and the like cases, production of a multiplicity of small recessed portions 61 with a diameter of 1 to 50 μm and a depth of 1 to 50 μm in the dots 63 of the irregular reflection portion 10 is effective for achieving efficient radiation of the excitation beam through the light radiating surface 8. At the same time, this has the effect of reducing the area proportion of the flange portions 62, which hampers the transmission of fluorescent light to the photodetector and does not show irregular reflection of the excitation beam, based on the light transmitting surface 9. As a result of this, the area for intercepting the fluorescent light on the light transmitting surface 9 can be reduced, and the fluorescent light can be efficiently transmitted to the photodetector. In addition, it is also effective to preliminarily produce large recessed portions 61 and to produce a multiplicity of smaller recessed portions 61 in the large recessed portions 61.

In addition, the irregular reflection portion 10 may have a configuration in which a plurality of (at least two) recessed portions are produced, and the plurality of recessed portions are disposed in one dot so that the plurality of recessed portions are substantially covered with one reflection portion. In this case, also, each of the plurality of recessed portions preferably has a diameter of 1 to 50 μm and a depth of about 1 to 50 μm.

Figure 7:
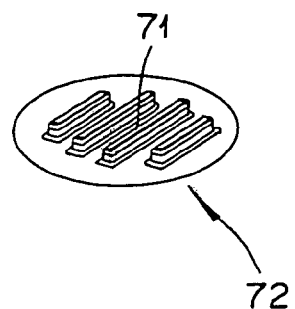
FIG. 7 is a perspective view showing only a dot portion constituting the irregular reflection portion which is formed at a light transmitting surface.

Further, in the case of the pattern of rectangular dots 51 shown in FIG. 5, parallel linear recessed portions 61 may be produced, or, as shown in the perspective view of only the dot portion in FIG. 7, linear recessed portions 71 may be provided in the inside of the dot 72. In the case where the linear recessed portions 71 are provided in the inside of the dot 72, the minimum width of the recessed portions 71 is suitably about 1 to 50 µm, and the depth of the recessed portions 71 is suitably 1 to 50 µm.

Incidentally, while the shape of the recessed portions 61 has been described as cylindrical or linear by way of example, it suffices for the depth of the recessed portions 61 to be so designed that the straight line drawn at a minimum incidence angle θ of the excitation beam being wave-guided against the normal drawn from an end portion of the flange portion 62 perpendicularly to the waveguide main body 6 would not make contact with the recessed portion 61 in any case, as has been described above referring to FIG. 6. Therefore, a method may be adopted in which conical recessed portions 61 with a comparatively large surface roughness are produced by a drill, sandblasting, or polishing, and smaller recessed portions 61 are formed in the inside of the recessed portions 61 by use of laser.

Figure 8:
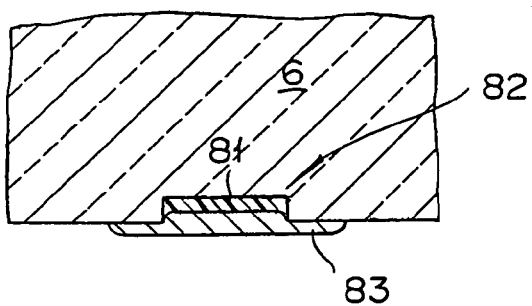
FIG. 8 is a sectional view showing the structure of a further embodiment of the irregular reflection portion.

Furthermore, the irregular reflection portion 10 may be formed by a method in which, as shown in the sectional view of FIG. 8, a coating material 81 having a high refractive index and admixed with particulates of titanium oxide, alumina, or other metal, hollow glass particles or the like having a high refractive index is applied to the inside of recessed portions 82, and a metallic film 83 is formed on the coating by vapor deposition or sputtering. As a result, the inside of the recessed portions 82 is filled with a mixed material prepared by mixing the coating material which is a transparent material higher in refractive index than the waveguide main body 6 with a particulate metallic material different in refractive index from the transparent material. In such a method, the inside of the recessed portions 82 is filled with the coating material admixed with the particulates, whereby efficient irregular reflection can be achieved, as contrasted to the case where synthetic quartz is etched by use of carbon fluoride, whereby the bottom portions of the recessed portions 82 are liable to become smooth flat surfaces having comparatively little and few projections and recesses, so that irregular reflection of wave-guided light is difficult to achieve.

Furthermore, the light waveguide 1 has a mirror portion 11 for reflecting the wave-guided light, in the vicinity of the portion of a side surface other than the light radiating surface 8, the surface including the light transmitting surface 9, and the light introducing portion 3 of the waveguide main body 6 (FIG. 1). The mirror portion 11 is a reflective member, and can be produced, for example, simultaneously with the vapor deposition or sputtering step in producing the irregular reflection portion, or by applying a mirror coating material. This ensures that the light wave-guided without being radiated out of the waveguide main body 6 is reflected by the mirror portion 11, and is again wave-guided in the direction of the light radiating surface 8, so that the light can be efficiently utilized as the excitation beam.

While the mirror portion 11 is drawn in the vicinity of a surface perpendicular to the light wave-guiding direction of the waveguide main body 6 in FIG. 1, the side surface may be inclined by an angle of about 1 to 5 degrees against the vertical.

In addition, the mirror portion 11 may be provided at a waveguide main body surface in the vicinity of the boundary between the light separation portion 5 and the light transmitting surface 9, whereby the accuracy on a production step basis can be enhanced.

Furthermore, the light waveguide 1 may include a layer of a transparent blank material lower in refractive index than the blank material of the waveguide main body 6, on at least the light separation portion 5 and the light transmitting surface 9, of the surfaces of the waveguide main body 6. This ensures that the amount of the light absorbed by the light separation portion 5, of the light introduced through the light introducing portion 3, is reduced, whereby the amount of the light which can be wave-guided can be increased.

The angle of the light introduced through the light introducing portion 3 can be preliminarily set in the form of being subtracted by the angle of the light absorbed by the light separation portion 5, by use of a lens or the like. For this purpose, for example, the end face of the waveguide main body 6 at the light introducing portion 3 is formed to be a convex lens.

However, the light waveguide 1 has an important target of being utilized for a small type fluorescent sensor, and, therefore, it desirably has a structure as simple as possible. Though it is easy to reduce the thickness of the waveguide main body 6 for a reduction in size, it becomes more difficult to form a lens accurately at the light introducing portion 3 as the waveguide main body 6 is made to be thinner. In this embodiment, an LED is used as the light source 2. The LED light makes it difficult to condense the light accurately and to control the incidence angle as in the case of a laser beam; therefore, for increasing the amount of light wave-guided, it is effective to provide a layer of a transparent material having a low refractive index. Such a structure is a general method in the cases of other light waveguides such as optical fibers, and the technology of adopting an inclined refractive index layer such that the refractive index is gradually lowered from the waveguide toward the outside is also known.

As a blank material for use in forming the layer of the transparent blank material, preferred is the fluoro-resin which has been used for forming the light separation portion 5; the fluoro-resin has shown good results when used for optical fibers, and, in this case, a coloring matter for absorbing the wave-guided light such as carbon black is not added to the resin.

Besides, where a glass is used for forming the waveguide main body 6, there may be adopted a method of coating a porous glass, and a method of doping the waveguide main body 6 with fluorine, other than the use of the fluoro-resin.

Here, the refractive indices of examples of the blank materials for use in forming the above-mentioned portions are collectively shown in Table 1 below.

TABLE 1

| Name of blank material | Product name or abbreviation thereof (producer name) | Refractive index |
|---|---|---|
| Amorphous fluoro-resin | CYTOP (Asahi Glass) | 1.34 |
| Fluoro coating agent | OPSTER (JSR) | 1.41 |
| | DYNEON THV (Sumitomo 3M) | 1.36 |
| Acrylic resin | DESOLITE (JSR) | 1.50–1.57 |
| Thermoplastic fluoro-resin | PFA | 1.35 |
| | PTFE | 1.35 |
| | FEP | 1.34 |
| | EFEP | 1.38 |
| | ETFE | 1.42 |
| | ECTFE | 1.43 |
| | PVDF | 1.42 |
| Cyclic polyolefin | ZEONOR (Zeon Corp.) | 1.53 |
| | ZEONEX (Zeon Corp.) | 1.525, 1.509 |
| Artificial quartz | AQ (Asahi Glass) | 1.456 |
| Borosilicate glass | BK7 (Schott) | 1.517 |

The refractive indices of the portions are in the relationship of [the refractive index of the waveguide main body 6]>[the refractive index of the material in contact with the light radiating surface 8 (i.e., the analyte-containing liquid or the hydrogel containing the liquid) and the refractive index of the absorption layer 4]>[the refractive index of the material in contact with the light transmitting surface 9]. This can be expressed in terms of total reflection angles of guidable light incident on the boundaries between the portions, as [the total reflection angle at the light transmitting surface 9]<[the total reflection angle at the light radiating surface 8 and the total reflection angle at the light separation portion 5].

In the next place, the action of the light waveguide will be described.

In the light waveguide 1 having the structure as above-described, the light introduced through the light introducing portion 3 is first incident on the light separation portion 5 provided with the absorption layer 4 which basically does not transmit light therethrough and is lower in refractive index than the waveguide main body 6. In this case, the beams a, b, c incident on the interface at angles of not less than the total reflection angle determined by the refractive indices of the waveguide main body 6 and the absorption layer 4 can be wave-guided while undergoing total reflection inside the waveguide at the light separation portion 5. On the other hand, the light d incident at an angle smaller than the total reflection angle is mostly transmitted to the absorption layer 4 side, so that it is rapidly attenuated and is substantially absorbed before reaching the light radiating surface 8 or the light transmitting surface 9. As a result, as to the reflection angle α inside the waveguide main body 6 of the light components capable of reaching the light radiating surface 8 or the light transmitting surface 9, the minimum is determined by the refractive indices of the absorption layer 4 and the waveguide main body 6. The light wave-guided at an angle slightly smaller than the minimum of the reflection angle α is liable to be wave-guided with little attenuation. In the present invention, the absorption layer 4 having a refractive index ($n2$) higher than the refractive index ($n3$) of the material in contact with the light transmitting surface 9 is provided, whereby the reflection angle of the light capable of being wave-guided through total reflection in the region of the light transmitting surface 9 is made to be smaller than the above-mentioned reflection angle α. Therefore, the beams wave-guided at angles slightly smaller than the reflection angle α can also be prevented from outgoing through the light transmitting surface 9, so that the incidence of the excitation beam on the photodetector can be restrained more securely.

A portion b of the totally reflected light wave-guided inside the waveguide main body 6 by the light separation portions 5 is supplied to the irregular reflection portion 10, where its reflection angle is changed, and it is radiated through the light radiating surface 8. Of the light wave-guided at angles of not less than the total reflection angle, the light components a and c not having impinged on the irregular reflection portion 10 are, on the light radiating surface 8 side, partly radiated out of the waveguide in the case where the refractive index of the absorption layer 4 is equal to or smaller than the refractive index of the material in contact with the light radiating surface 8. On the other hand, on the light transmitting surface 9 side, the light components a and c undergo total reflection and cannot pass through the light transmitting surface 9, since the light transmitting surface 9 is in contact with the material having a refractive index lower than the refractive index of the absorption layer 4.

Meanwhile, when the beam b having been changed in reflection angle by the irregular reflection portion 10 and radiated through the light radiating surface 8 is reflected by the light radiating surface 8, the light reflected according to the reflectance determined by the refractive indices of the waveguide main body 6 and the material in contact with the light radiating surface 8 is sent back to the light transmitting surface 9 side, and this light can pass through the light transmitting surface 9 to reach the photodetector. However, the amount of this light is part of the angular components of the light being wave-guided, and, further, it depends on the reflectance determined by the refractive index of the waveguide main body 6 and the refractive index of the material in contact with the light radiating surface 8, so that this light can be sufficiently attenuated by an optical filter or the like before being incident on the photodetector. As the optical filter, one through which fluorescent light is transmitted favorably but the excitation beam is transmitted with difficulty can be selected. If the optical filter is in contact with the waveguide main body 6 at the light transmitting surface 9, the excitation beam may leak there to the photodetector side. In the structure according to the present invention, however, the irregular reflection portion 10 functions as a spacer between the waveguide main body 6 and the optical filter, so that the leakage of the excitation beam due to the contact can be prevented.

On the other hand, the light coming from the light radiating surface 8 will, in most cases, pass directly through the light transmitting surface 9 to the outside. Therefore, the light such as fluorescent light entering from the light radiating surface 8 side passes through the light waveguide 1 to enter the photodetector.

Thus, the light waveguide 1 can radiate light only from the light radiating surface 8 and can cause the external light entering from the light radiation direction to pass therethrough in the direction opposite to the light radiation direction.

Incidentally, where the light waveguide 1 is connected to a photodetector such as a photodiode in a fluorescent sensor, the periphery of a light receiving portion of the photodetector is preferably connected in close contact in the vicinity of the light separation portion 5 near the boundary between the light separation portion 5 and the light transmitting surface 9. In addition, a housing for separation between an analyte-containing liquid and electronic devices such as photodiode and LED inside the photodetector is connected to the light separation portion 5 on the light radiating surface 8 side.

Figure 9:
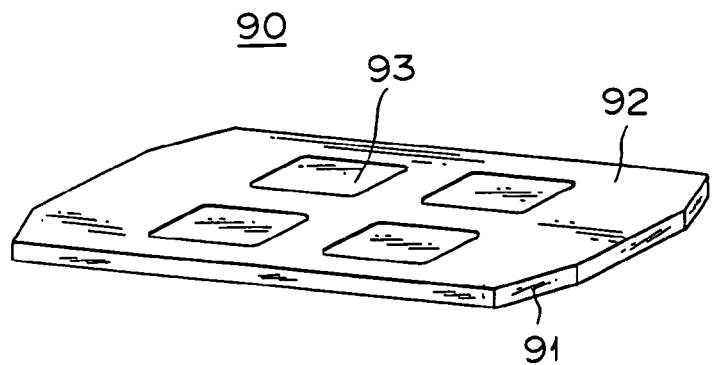
FIG. 9 is a perspective view showing another embodiment of the light waveguide to which the present invention is applied.

While one embodiment of the light waveguide according to the present invention has been described above, the description has been made of the configuration in which one light radiating surface 8 and one light transmitting surface 9 are provided and a single light introducing portion 3 is provided in a waveguide main body 6. However, the present invention is not limited to such a structure, and pluralities of light radiating surfaces and light transmitting surfaces and, further, light introducing portions may be provided. For example, a light waveguide 90 as shown in FIG. 9 may be formed in which four light radiating surfaces 93 are provided in a surface on one side of a decahedral waveguide main body, four light transmitting surfaces are provided in a surface on the opposite side, and four faces of the decahedron are made to be light introducing portion 91. In this case, the portions other than the light radiating surfaces 93, the light transmitting surfaces, and the light introducing portions 91 are light separation portions 92 which are each covered with an absorption layer.

Figure 10:
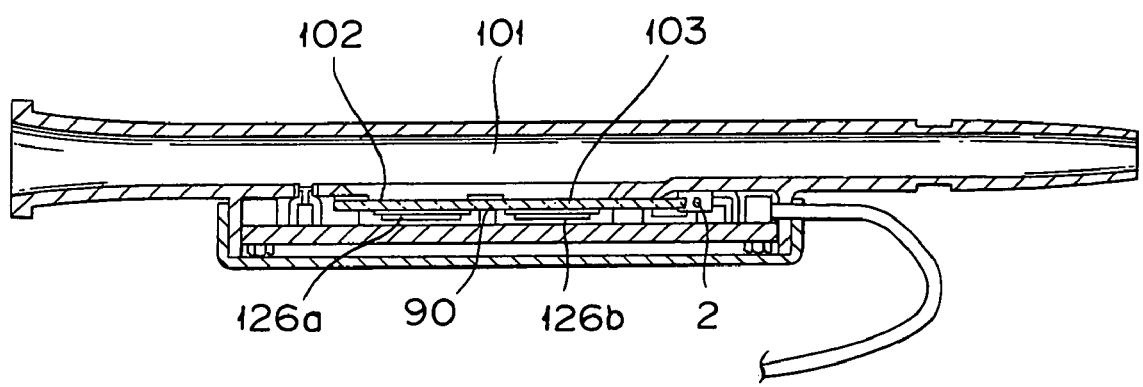
FIG. 10 is a sectional view showing an example of sensor structure using the light waveguide.

With the pluralities of light radiating surfaces 93, light transmitting surfaces and light introducing portions 91 thus provided, for example, as shown in the sectional view of FIG. 10, indicator layers (not shown) for showing fluorescence upon bonding respectively with different analytes are provided respectively at a first light radiating surface 102 and a second light radiating surface 103 directed to the inside of a passage 101 in which a liquid flows, and a plurality of corresponding photodetectors 126a and 126b are provided on the light transmitting surface side, whereby a plurality of analytes present in the liquid flowing in the passage 101 can be simultaneously measured by a single fluorescent sensor. In addition, an indicator layer not containing any substance that shows fluorescence upon bonding with an analyte may be provided at the second light radiating surface 103, whereby the measurement accuracy can be enhanced.

[Fluorescent Sensor]

Now, an embodiment of a fluorescent sensor using the above-described light waveguide 1 will be described below. This sensor is an embedded-in-body type sensor.

Figure 11:
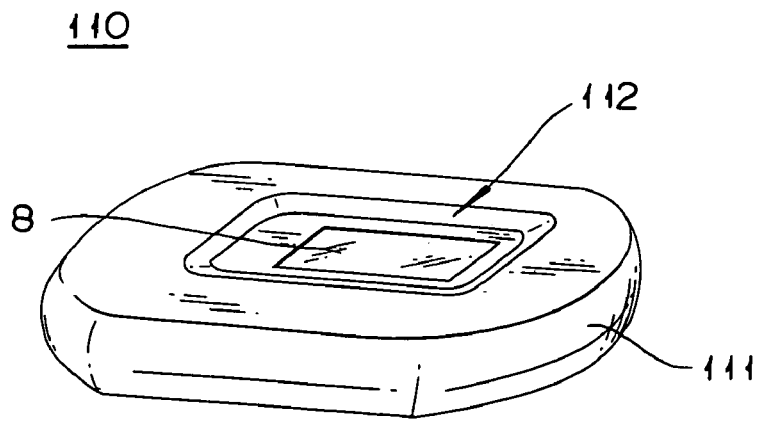
FIG. 11 is a perspective view of a fluorescent sensor to which the present invention is applied.
Figure 12:
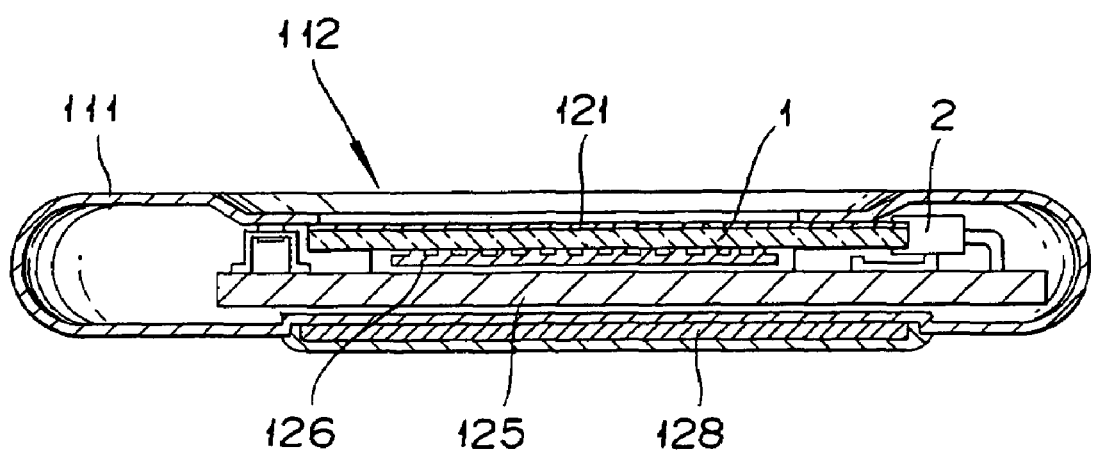
FIG. 12 is a sectional view of the fluorescent sensor.

FIG. 11 is a perspective view of a fluorescent sensor to which the present invention is applied, and FIG. 12 is a sectional view of the fluorescent sensor.

The fluorescent sensor 110 is arranged in a sealed housing 111 so that a light radiating surface 8 of a light waveguide 1 can make contact with the exterior through at least one window portion 112. The material of the housing 111 may be any one inasmuch as it does not produce any problem on the basis of the function as the embedded-in-body type sensor. As the material, stainless steel and titanium are preferable.

On the light radiating surface 8, an indicator layer 121 (not shown in FIG. 11; see FIG. 12) composed of a hydrogel bonded to fluorescent indicator molecules for showing fluorescence upon reacting with an analyte in a humor in a living body is fixed to at least one light radiating surface 8. The indicator layer 121 brought into contact with the humor in the living body so as to sense the concentration of the analyte is bonded to the light radiating surface 8 exposed through the window portion 112. Incidentally, where a plurality of light radiating surfaces are provided, different indicator layers 112 may be respectively disposed there, as above-mentioned.

In the housing 111, other than the light waveguide 1, a light source 2 such as an LED is disposed at an end portion of the light waveguide 1, a substrate 125 is provided on the side of a light transmitting surface 9 of the light waveguide 1, with a predetermined spacing therebetween, and a photodetector 126 such as a photodiode is disposed on the substrate 125. Particularly, the photodetector 126 is so disposed as to receive only the light coming from a light transmission passage and not to pick up the stray light present inside the housing 111.

In addition, though not shown, the substrate 125 is provided thereon with an integrated circuit for processing a signal from the photodetector 126, a transmitter for transmitting a signal to the exterior, a battery as a power source, etc. In addition, an antenna 128 for outputting the signal from the transmitter to the exterior is provided on the outside of the housing 111. Further, if necessary, a temperature sensor for enhancing data accuracy is disposed. Besides, an amplifier for amplifying the signal from the photodetector may be provided, as required.

The housing 111, exclusive of the window portion 112, is so designed as to maintain a liquid-tight condition so that these members would not make contact with a liquid. Particularly, the window portion 112 is sufficiently packed with a resin material or the like so that a liquid would not enter the interior through this portion.

In the fluorescent sensor 110, the signal from the photodetector 126 (together with a signal from a temperature sensor, if any) is processed by and accumulated in the integrated circuit, to be outputted to an external system through the antenna 128 at appropriate times. Incidentally, the antenna 128 itself is also preferably provided in the state of being covered with a resin or the like for preventing an antenna coil or the like from making contact with the humor.

When the fluorescent sensor 110 is left indwelling in a living body, the inside of the indicator layer 121 is put into an equilibrium condition with the analyte concentration in the humor in the living body. As a result, the indicator molecules present in the indicator layer 121 and the analyte are brought into a coupling/dissociation reaction, whereby the intensity of fluorescence in the indicator layer 121 is varied. The varied fluorescence intensity is detected by the photodetector 126 and converted into an electrical signal, which is transmitted to the extracorporeal system.

In the fluorescent sensor 110 configured as above, the light from the light source 2 can be guided as an excitation beam to only the indicator layer 121 side by the light waveguide 1 provided between the photodetector 126 and the indicator layer 121, so that the hydrogel in the indicator layer 121 can be evenly irradiated with the excitation beam, and measurement of fluorescence can be performed. Therefore, since the utilization efficiency of the light from the light source 2 is good, an LED as small as possible in size and as small as possible in power consumption can be used, so that a reduction in the size of the fluorescent sensor 110 can be achieved. In addition, since the light waveguide 1 guides the excitation beam, transmits the fluorescent light from the indicator layer 121 to the photodetector 126, and prevents stray light or the like from entering, an enhancement of sensitivity as fluorescent sensor can also be achieved.

Figure 13:
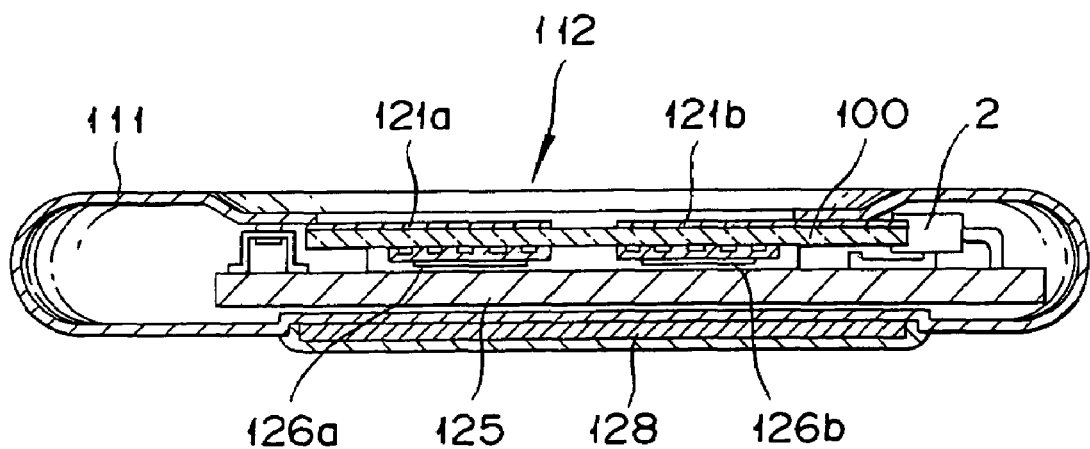
FIG. 13 is a sectional view showing another embodiment of the fluorescent sensor to which the present invention is applied.

FIG. 13 is a sectional view showing another embodiment of the fluorescent sensor to which the present invention is applied.

In this embodiment, use is made of a light waveguide 1 is provided with a plurality of (in the figure, two) light radiating surfaces and a plurality of (in the figure, two) light transmitting surfaces disposed opposite to the light radiating surfaces. As for indicator layer, therefore, different indicator layers 121a and 121b are mounted respectively on the light radiating surfaces. Besides, on the light radiating surface side, two photodetectors 126a and 126b for individually detecting the fluorescent beams coming from the indicator layers 121a and 121b are provided. The indicator layer 121b is obtained by omitting a fluorescent substance for measurement of an analyte from the indicator layer 121a, to serve as a reference layer.

As for the outlook configuration, like the one shown in FIG. 11, the housing 111 is provided with the single window portion 112, through which two indicator layers 121a and 121b mounted on the two light radiating surfaces of the light waveguide 100 are exposed. Incidentally, one light source 2, one substrate 125, one antenna 128, as well as one integrated circuit, one power source and the like single components are provided.

Thus, in this light waveguide 100, by only providing the single light waveguide 100 with pluralities of light radiating surfaces and light transmitting surfaces and correspondingly providing the plurality of indicator layers 121a and 121b and the plurality of photodetectors 126a and 126b, the measurement accuracy can be enhanced and a plurality of analytes can be detected at a time, notwithstanding the housing 111 and the like component members are single. In this case, moreover, the window portion 112 provided in the housing 111 for exposing the indicator layers may also be single.

Incidentally, while an example in which two light radiating surfaces and two light transmitting surfaces are provided has been shown in the light waveguide 100 shown in FIG. 13, this is not limitative, a light waveguide provided with larger numbers of light radiating surfaces and light transmitting surfaces can also be used. In addition, while different indicators are provided respectively on a plurality of light radiating surfaces in the case of detecting different analytes, this is not limitative, and the same indicator layer may be mounted on each of a plurality of light radiating surfaces.

The fluorescent sensors (configurations shown in FIGS. 12 and 13) described above are mere examples for illustrating the present invention, and are not limitative; for example, the present invention is applicable also to an apparatus which does not have a battery and in which measurement is conducted by supplying electric power to internal electric circuits such as a light source 2 and an integrated circuit from an extracorporeal system each time of measurement.

In addition, a configuration may be adopted in which an integrated circuit portion and a battery are mounted in an extracorporeal system, and are communicated to the inside of a living body through lead wires, and the antenna coil is omitted.

Besides, as an electrical signal transfer means other than electromagnetic waves, a faint high-frequency current may be passed through a body tissue between an embedded-in-body type sensor and an extracorporeal system.

As for the size of the fluorescent sensor 110, one of the type of comprising the battery and the antenna 128 can be produced to have a length of 10 to 50 mm, a width of 3 to 20 mm, and a thickness of 2 to 10 mm, whereas one of the type free of battery can be produced to have a length of 5 to 20 mm, a width of 2 to 5 mm, and a thickness of 0.5 to 3 mm.

It is obvious that the size can be changed by variation in the characteristics of fluorescence arising from the interaction between the indicator molecules and the analyte(s), the amounts of electric power supplied to the excitation beam source and the electrical circuits, a safety mechanism operative upon occurrence of a mechanical problem, design of an electronic circuit portion for calculating the measured values and transmitting an alarm signal to an extracorporeal system by the detector itself, and the like.

Now, examples of the light waveguide according to the present invention will be described below.

EXAMPLE 1

Example 1 pertains to a light waveguide 1 using a synthetic quartz plate (0.7 mm thick, 20 mm wide, 30 mm long; refractive index: 1.46; produced by Asahi Glass Co., Ltd.) as a waveguide main body 6.

In producing the light waveguide, first, a PET-based masking tape was adhered to one side of the synthetic quartz glass, and the masking tape was perforated. The holes were opened in the PET surface at a position spaced by at least 5 mm from an end portion of the synthetic quartz plate and in a 10 mm×10 mm region by use of an excimer laser. The holes had a diameter of 0.2 mm. The number of the holes opened in the 10 mm×10 mm region was 95, with a hole center interval of 1 mm.

In this case, masking may be conducted by use of a urethane resin dope or a styrene-based resin dope in place of the PET-based making tape, and only the resin portion may be similarly perforated by the excimer laser. Besides, the hole diameter can be controlled within the range of from 1 μm by regulating the mask hole diameter in use of the excimer laser.

Subsequently, the perforated masked surface of the synthetic quartz plate was subjected to ion etching with $CF_4$ at 750 W for 80 min by use of a reactive etching apparatus (IE-4800, produced by Samco International, Inc.), to form recessed portions 61 with a depth of 5 μm and a diameter of 200 μm. Incidentally, it was possible to produce recessed portions directly in a synthetic quartz plate masked with a styrene-based resin dope or a metal by irradiating the quartz plate with excimer laser from the back side.

Subsequently, after the mask was removed, a film of aluminum was formed in a thickness of 1 μm on the whole area of the recessed portion provided surface of the synthetic quartz plate and the whole areas of side faces of the synthetic quartz plate by sputtering by use of a sputtering apparatus (for example, SPF-210H, produced by Anelva Corporation, or SPH-306C, produced by Showa Shinku Co., Ltd.).

The formation of the metallic film by sputtering may be carried out by DC sputtering or RF sputtering. Here, the film was formed by use of SPH-306C (RF sputtering) under the following conditions. Reverse sputtering was conducted under the conditions of an Ar gas flow rate of 100 sccm, a pressure of $7 \times 10^{-3}$ Torr (0.9333 Pa), a power of 400 W, and a time of 5 min. Presputtering was conducted under the conditions of an Ar gas flow rate of 50 sccm, a pressure of $3 \times 10^{-3}$ Torr (0.400 Pa), a power of 350 W, and a time of 15 min. A film thickness of 1 μm was obtained by a film formation time of 15 min per sheet by opening the shutter. Incidentally, for enhancing the adhesion property, it is desirable to form the film at a substrate temperature of not less than 100° C. It was possible to easily form the metallic film by use of gold, chromium, or silver as the metal.

Next, a negative type photoresist (OMR-83 60CP, produced by Tokyo Ohka Kogyo Co., Ltd.) was applied to the vapor deposition surface of the synthetic quartz plate by spin coating, and irradiation with UV rays was conducted by masking so as to cover the recessed portions 61, to achieve a resin masking with a diameter of 0.3 mm. Simultaneously, the side faces were also masked, then washing in a solvent was conducted to remove the uncured resin layer, and baking at 140° C. was conducted to cure the resin. Thereafter, the exposed aluminum layer was removed by washing in an etching solution (phosphoric acid:nitric acid:acetic acid:water=16:1:2:1) heated to 40° C., to produce an irregular reflection portion 10 and side face mirror portions. Then, the quartz plate was immersed in phenol (stripper 502A, produced by Tokyo Ohka Kogyo Co., Ltd.) heated to 120° C. for 10 min, immersed in a strip rinse liquid (produced by Tokyo Ohka Kogyo Co., Ltd.) for 5 min, IPA substitution was conduced for 5 min. and washing in ultra-pure water was conducted, to remove the masking material.

Incidentally, the aluminum layers can be produced also by applying a commercially available mirror ink. It should be noted here, however, that in view of the properties of the mirror ink, attention should be paid to the washing liquid and the like so as not to dissolve the mirror ink during the subsequent processing or washing. Besides, in the case of utilizing a light source 2 with a wavelength corresponding to a bad reflectance, it is preferable not to select the mirror ink, and a method of adhering a metal such as aluminum and gold by sputtering or vapor deposition is more convenient for the subsequent processing.

After the synthetic quartz plate was thus provided with the irregular reflection portion 10, a 12 mm×12 mm PET-based masking tape was adhered to the plate so as to completely cover the irregular reflection portion 10, and is adhered also to the synthetic quartz plate surface on the opposite side of the irregular reflection portion 10 in a corresponding form, to protect the window portion 112. Next, a 10% amorphous fluoro-resin dope (produced by Asahi Glass Co., Ltd.; refractive index: 1.34) admixed with 4% carbon black (produced by Cabot Corporation) was applied four times to the whole surface area of the synthetic quartz plate by dip coating, to produce an absorption layer 4 in a thickness of 100 μm. The refractive index of the absorption layer 4 was calculated to be 1.35 through 1.36 from the measurement of refractive index by the surface plasmon resonance method with a dispersion prepared by dispersing carbon black in water and fluorocarbon solution (produced by 3M Company).

Next, by use of a rotating grindstone, one of the side faces of the synthetic quartz plate was ground off until the quartz surface was exposed, and the surface was polished with a 0.1 micrometer lapping film, to produce a light introducing portion 3. Finally, the masking on the window portion 112 was removed, followed by washing, to complete the light waveguide 1.

In the light waveguide 1 thus produced, the absorption layer 4 formed of the amorphous fluoro-resin was well durable to organic solvents such as acetone, and was therefore easy to wash. Besides, the coverage of the light transmitting surface 9 with aluminum was 6.7%.

Furthermore, when light from an LED (produced by Sander Electronic Co., Ltd.; 395 nm) was introduced into the light introducing portion 3 of the light waveguide 1 produced as above, the scattering of the wave-guided light from the side surfaces of the recessed portions in the irregular reflection portion 10 was observed through the light radiating surface at the window portion 112. Besides, in this light waveguide 1, scattered light could not be recognized directly from the side of the light transmitting surface 9 at any angle. As for the irregular reflection locations of the irregular reflection portion 10, the light at peripheral side surfaces of the cylindrical recessed portions 61 could be recognized well, while the irregular reflection at the bottom surfaces of the recessed portions 61 could not substantially recognized.

EXAMPLE 2

Example 2 pertains to a light waveguide produced by use of a borosilicate glass plate (produced by Schott Corporation) having the same dimensions as those of the synthetic quartz plate shown in Example 1 as the waveguide main body 6.

In producing the light waveguide, first, excimer laser (KrF; 280 mJ, 80 shots, 100 Hz) was radiated directly to the borosilicate glass plate, to produce holes with a hole diameter of 300 μm in the same pattern as in Example 1. The holes constitute recessed portions 61, the depth of which was 30 through 40 μm.

Subsequently, aluminum was sputtered by the same process as in Example 1, to produce an irregular reflection portion 10 with a diameter of 400 μm. The coverage of the light transmitting surface 9 with aluminum was 12%.

In Example 2, also, like in Example 1, the scattering of the wave-guided light from the whole area of the recessed portions 61 in the irregular reflection portion 10 could be recognized through the light radiating surface at the window portion 112. In addition, the scattered light could not be recognized directly from the side of the light transmitting surface 9 at any angle. Unlike in Example 1, the recessed portions 61 produced directly by the laser were not cylindrical in shape but were in the shape of domes deeper at center, and, as a result, efficient reflection of the excitation beam in the whole area of the recessed portions 61 was achieved.

EXAMPLE 3

Example 3 pertains to a fluorescent sensor 110 having a single window portion 112, produced by use of the light waveguide 1 produced in Example 2.

First, a light source 2 was disposed at a predetermined position in a housing 111, and was connected to the light waveguide 1. To obtain the light source 2, a 5 mmφ shot-type LED (produced by Sander Electronic Co., Ltd.) was machined so as to facilitate connection thereof to a side face of the waveguide, was adhered to a predetermined position in the housing by use of a commercially available black adhesive, and was connected to the light waveguide 1. In addition, a commercially available precision measurement photodiode (produced by Hamamatsu Photonics K.K.) with a 10 mm×10 mm measurement surface was connected to the absorption layer 4 in the periphery of the light transmitting surface of the light waveguide 1, with a commercially available optical filter (SC42; produced by Fuji Photo Film Co., Ltd.) therebetween, by use of a carbon black-containing amorphous fluoro-resin dope as an adhesive.

The light waveguide 1 showed an excitation beam amount of 48 μW/cm$^2$ from the light radiating surface 8 when a fixed current of 20 mA was passed.

In producing the light radiating surface 8, after treatment with an ethanol solution of 3-acryloxypropyltrimethoxysilane, an aqueous solution containing 10 w/w % of 9,10-bis[N-[2-(5,5-dimethylborinan-2-yl)benzyl]-N-[6'-[(acryloylpolyethyleneglycol-3400)carbonylamino]-n-hexylamino]methyl]-2-acetylanthracene (hereinafter referred to as F-PEG-AAm), 15 w/w % of acrylamide, and 1 w/w % of ethylene bisacryalamide was brought into polymerization, to form a fluorescent indicator layer in a thickness of 50 μm.

In this Example 3, when a fixed current of 20 mA was passed to the LED to cause fluorescence, and the fluorescent light from the indicator layer 121 was compared between a glucose-free phosphoric acid buffer (pH 7.4) and a 500 mg/dl glucose-containing phosphoric acid buffer (ph 7.4), a difference in current flowing in the photodiode of 33 nA was obtained. This fluorescence could be sufficiently measured even with 0.1 sec light emission. Thus, a fluorescent sensor could be produced which is capable of measuring the glucose concentration in a liquid, not only with continuous light emission but also with such a small power consumption as to cause light emission for only about 0.1 sec per 1 min.

In addition, in such a fluorescent sensor, a light radiating surface 8 having an indicator layer 121 not containing F-PEG-AAm can easily be disposed in the same light waveguide 1, for the purpose of removing faint stray light components and the fluorescent components other than the analyte in the analyte-containing liquid under examination. By use of the fluorescence value F1 from the light radiating surface 8 not containing the fluorescent indicator layer 121 and the fluorescence value F0 at glucose concentration 0 of the indicator layer 121 containing F-PEG-AAm preliminarily measured by use of the phosphoric acid buffer, and by use of F0+F1 as a base, a normally varying glucose concentration can also be measured.

The light waveguide according to the present invention has the functions of radiating light in one direction and, simultaneously, transmitting light in the direction opposite to the light radiation direction. Therefore, the light waveguide can be used for an apparatus which utilizes such light waveguide performance.

Besides, the fluorescent sensor according to the present invention can be utilized for detecting and measuring an analyte in a living body, continuously or intermittently, by embedding the sensor in the living body.

This application is based on Japanese Patent Application No. 2004-318094 filed on Nov. 1, 2004, the contents of which are hereby incorporated by reference.

What is claimed is:

1. A light waveguide comprised of a light transmitting material, said light waveguide comprising:
   a light introducing portion for introducing light coming from a light source;
   a light radiating surface for radiating the light introduced through said light introducing portion;
   a light transmitting surface which is opposed to said light radiating surface and through which at least a portion of external light incident from said light radiating surface is transmitted to the exterior;
   an irregular reflection portion provided on said light transmitting surface to change the reflection angle of light on said light transmitting surface; and
   a light separation portion provided on a surface in a region ranging from said light introducing portion to said light radiating surface and said light transmitting surface, said light separation portion having an absorption layer formed of a material having a refractive index lower than the refractive index of said light transmitting material and higher than the refractive index of a material in contact with said light transmitting surface.

2. The light waveguide according to claim 1, satisfying the relationships of n1>n2+0.01 and n2>n3+0.01, where n1 is the refractive index of said light transmitting material, n2 is the refractive index of said absorption layer, and n3 is the refractive index of said material in contact with said light transmitting surface.

3. The light waveguide according to claim 1, having the relationship of the following formula (1), and t1 in the formula (1) is greater than 1:

$$X = t1 \times L \times \mathrm{Tan}(\mathrm{Sin}^{-1}(n2/n1)) \quad (1),$$

where L is the thickness of said light waveguide, and X is the length from the light transmitting surface and said light radiating surface to said light introducing portion.

4. The light waveguide according to claim 1, wherein said absorption layer is formed of an amorphous fluoro-resin containing 0.1 to 10 mass % of carbon black.

5. The light waveguide according to claim 1, wherein said irregular reflection portion comprises:
   a particulate mixed transparent layer in which particulates different in refractive index from a transparent material higher in refractive index than said light transmitting material are mixed in said transparent material; and
   a reflection layer which is provided so as to hide said particulate mixed transparent layer from the exterior and which does not transmit but reflect light.

6. The light waveguide according to claim 1, wherein said irregular reflection portion comprises:
   at least one recessed portion provided at a portion on said light transmitting surface; and
   a reflection portion provided so as to hide said recessed portion from the exterior;
   said recessed portion provided at a position excluding the inside of a waveguide formed at an angle b from an end portion of a light reflecting portion relative to a line perpendicular to said light transmitting surface, where b is the minimum incidence angle of the light being guided on said light transmitting surface.

7. The light waveguide according to claim 6, wherein said recessed portion is in a roughly cylindrical shape with a diameter of 1 to 50 μm and a depth of 1 to 50 μm.

8. The light waveguide according to claim 6, wherein at least two said recessed portions are provided, and said at least two recessed portions are covered by one reflection portion.

9. The light waveguide according to claim 8, wherein said at least two recessed portions are each in a roughly cylindrical shape with a diameter of 1 to 50 μm and a depth of 1 to 50 μm.

10. The light waveguide according to claim 6, wherein said recessed portion is filled with a mixed material obtained by mixing a transparent material higher in refractive index than said light transmitting material with particulates different in refractive index from said transparent material.

11. The light waveguide according to claim 1, wherein said light radiating surface, said light transmitting surface, said light separation portion, and said light introducing portion are provided in a waveguide main body formed of a transparent material; and
   the other portion of said waveguide main body than said light radiating surface, said light transmitting surface, said light separation portion, and said light introducing portion is covered by a reflective material which does not transmit but reflect light.

12. The light waveguide according to claim 1, wherein said light separation portion and said light transmitting surface further have a transparent layer lower in refractive index than said light transmitting material.

13. The light waveguide according to claim 1, wherein a plurality of said irregular reflection portions are provided on said light transmitting surface, and the minimum distance between the adjacent irregular reflection portions is within two times the distance between said light transmitting surface and said light radiating surface.

14. A fluorescent sensor comprising:
   a light waveguide as set forth in claim 1;
   a light source for radiating an excitation beam to a light introducing portion of said light waveguide;
   an indicator layer provided in close contact with said light radiating surface of said light waveguide and comprising a hydrogel containing fluorescent indicator molecules which show a variation in fluorescent characteristics by reversibly bonding with an analyte; and
   a photo-detector provided at a position opposite to said light transmitting surface of said light waveguide for converting fluorescent light from said indicator layer into an electrical signal.

15. The fluorescent sensor according to claim 14, wherein said light waveguide, said light source, and said indicator layer are covered by a housing which contains them in the inside thereof and holds the inside thereof in a liquid-tight condition; and
   said light waveguide is disposed in said housing with said light radiating surface directed outwards.

16. The fluorescent sensor according to claim 14, wherein said fluorescent sensor is embedded in a living body for measuring a specified analyte in said living body.

* * * * *